United States Patent
O'Shea et al.

(10) Patent No.: US 11,232,373 B2
(45) Date of Patent: *Jan. 25, 2022

(54) SYSTEM AND USER INTERFACE FOR ACQUISITION AND STORAGE OF PATIENT MEDICAL INSURANCE DATA

(71) Applicant: CERNER INNOVATION, INC., Kansas City, KS (US)

(72) Inventors: Daniel P O'Shea, Downingtown, PA (US); Nicholas R Revak, Downingtown, PA (US)

(73) Assignee: CERNER INNOVATION, INC., Kansas City, KS (US)

( * ) Notice: Subject to any disclaimer, the term of this patent is extended or adjusted under 35 U.S.C. 154(b) by 108 days.

This patent is subject to a terminal disclaimer.

(21) Appl. No.: 16/531,724

(22) Filed: Aug. 5, 2019

(65) Prior Publication Data
US 2019/0354900 A1 Nov. 21, 2019

Related U.S. Application Data

(63) Continuation of application No. 12/173,519, filed on Jul. 15, 2008, now Pat. No. 10,410,141.
(Continued)

(51) Int. Cl.
*G16H 10/60* (2018.01)
*G06Q 10/00* (2012.01)
(Continued)

(52) U.S. Cl.
CPC ............ *G06Q 10/00* (2013.01); *G06Q 40/08* (2013.01); *G06Q 50/00* (2013.01); *G16H 10/60* (2018.01)

(58) Field of Classification Search
CPC .................................................. G16H 10/60
See application file for complete search history.

(56) References Cited

U.S. PATENT DOCUMENTS 5,077,666 A 12/1991 Brimm et al.
5,202,977 A 4/1993 Pasetes et al.
(Continued)

OTHER PUBLICATIONS

Health Plan Eligibility Benefit Inquiry and Response; CMS.org (Year: 2020).*
(Continued)

*Primary Examiner* — John A Pauls
(74) *Attorney, Agent, or Firm* — Shook, Hardy & Bacon L.L.P.

(57) ABSTRACT

A system is integrated with a hospital information system (HIS) to provide patient health insurance information identifying patient medical insurance eligibility coverage by sorting and parsing hatched electronic transaction message data to provide information to an HIS to facilitate accurate billing and account follow up. A system acquires patient medical insurance coverage identification data for use in medical reimbursement claim generation. An acquisition processor acquires medical insurance coverage information associating medical insurance coverage identifiers with corresponding patient identifiers for multiple different patients. A display processor initiates generation of data representing at least one display image for presenting an acquired medical insurance coverage identifier and corresponding patient identifier and enabling a user to initiate storage of the medical insurance coverage identifier in a record associated with the patient identifier in a healthcare information system. A communication processor initiates communication of the medical insurance coverage identifier for storage in the record associated with the patient identifier in a healthcare information system in response to a command received using the at least one display image.

20 Claims, 8 Drawing Sheets

Related U.S. Application Data (60) Provisional application No. 60/952,045, filed on Jul. 26, 2007.

(51) Int. Cl.
*G06Q 50/00* (2012.01)
*G06Q 40/08* (2012.01)

(56) References Cited

U.S. PATENT DOCUMENTS

| | | | |
|---|---|---|---|
| 5,253,164 | A | 10/1993 | Holloway et al. |
| 5,359,509 | A | 10/1994 | Little et al. |
| 5,523,164 | A | 6/1996 | Shibato et al. |
| 5,758,126 | A * | 5/1998 | Daniels .................. G06Q 40/04 715/780 |
| 5,915,241 | A | 6/1999 | Giannini |
| 5,950,169 | A | 9/1999 | Borghesi et al. |
| 6,341,265 | B1 | 1/2002 | Provost et al. |
| 6,343,271 | B1 | 1/2002 | Peterson et al. |
| 7,162,437 | B2 | 1/2007 | Shaak et al. |
| 7,370,018 | B2 | 5/2008 | Bryant et al. |
| 7,386,526 | B1 | 6/2008 | Chappel |
| 7,613,620 | B2 | 11/2009 | Salwan |
| 7,801,744 | B2 | 9/2010 | Patterson |
| 7,870,009 | B2 | 1/2011 | Patterson |
| 7,881,950 | B2 | 2/2011 | Patterson |
| 2002/0019754 | A1 | 2/2002 | Peterson et al. |
| 2002/0147867 | A1 | 10/2002 | Satlow |
| 2003/0069760 | A1 | 4/2003 | Gelber |
| 2003/0158760 | A1 | 8/2003 | Kannenberg |
| 2003/0191665 | A1 | 10/2003 | Fitzgerald et al. |
| 2003/0195771 | A1 | 10/2003 | Fitzgerald et al. |
| 2005/0086081 | A1 | 4/2005 | Brock-Fisher |
| 2005/0288964 | A1 * | 12/2005 | Lutzen .................. G16H 50/00 705/2 |
| 2006/0106941 | A1 * | 5/2006 | Singhal ............... H04L 67/2823 709/238 |
| 2006/0184397 | A1 | 8/2006 | Wester |
| 2007/0050219 | A1 | 3/2007 | Sohr et al. |
| 2007/0106607 | A1 | 5/2007 | Seib et al. |
| 2007/0228146 | A1 | 10/2007 | Rogers et al. |
| 2007/0260493 | A1 | 11/2007 | Dirienzo |
| 2008/0103826 | A1 | 5/2008 | Barrett |
| 2008/0228528 | A1 | 9/2008 | Keen et al. |
| 2014/0058757 | A1 | 2/2014 | Patterson |

OTHER PUBLICATIONS

Applicant Initiated Interview summary received for U.S. Appl. No. 12/173,519 , dated Sep. 28, 2016, 3 pages.
Applicant Initiated Interview Summary—received for U.S. Appl. No. 12/173,519 , dated Oct. 9, 2015, 3 pages.
Final Office Action received for U.S. Appl. No. 10/247,980, dated Sep. 25, 2007, 18 pages.
Final Office Action received for U.S. Appl. No. 10/253,223, dated Nov. 1, 2007, 17 pages.
Final Office Action received for U.S. Appl. No. 12/173,519 , dated Dec. 9, 2015, 12 pages.
Final Office Action received for U.S. Appl. No. 12/173,519 , dated Feb. 6, 2012, 14 pages.
Final Office Action received for U.S. Appl. No. 12/173,519 , dated Jul. 11, 2016, 13 pages.
Final Office Action received for U.S. Appl. No. 12/173,519 , dated Apr. 15, 2011, 15 pages.
International Search Report received for PCT Patent Application No. PCT/US2003/010191, dated Nov. 19, 2003, 2 pages.
Non-Final Office Action received for U.S. Appl. No. 10/247,980, dated Mar. 9, 2007, 16 pages.
Non-Final Office Action received for U.S. Appl. No. 10/253,223, dated Aug. 5, 2008, 3 pages.
Non-Final Office Action received for U.S. Appl. No. 10/253,223, dated Mar. 21, 2007, 19 pages.
Non-Final Office Action received for U.S. Appl. No. 12/173,519 , dated Mar. 11, 2016, 12 pages.
Non-Final Office Action received for U.S. Appl. No. 12/173,519, dated Dec. 20, 2010, 13 pages.
Non-Final Office Action received for U.S. Appl. No. 12/173,519 , dated Oct. 19, 2011, 14 pages.
Non-Final Office Action received for U.S. Appl. No. 12/173,519, dated Jul. 29, 2015, 7 pages.
Notice of Allowance received for U.S. Appl. No. 12/173,519, dated Apr. 29, 2019, 8 pages.

* cited by examiner

| | A | B | C | D | E | F | G | H | I | J | K |
|---|---|---|---|---|---|---|---|---|---|---|---|
| 1 | Compl | Coverage | Last Name | First Name | Patient # | Clinic Code | Insurance Code 1 | Insurance Code 2 | Acct Bal | Comments | |
| 2 | | | | | | | | | | | |
| 3 | | Active | HAYNES | LINDEN | 10747400 | 1 | C08 | A09 | 4384.75 | | |
| 4 | | Active | RICHARDSON | NATHANIAL | 10516292 | 1 | C01 | B20 | 4095.13 | | |
| 5 | | Active | RHODES | WES | 10705259 | 8 | B20 | C08 | 2240.73 | | |
| 6 | | Active | BROCK | RAND | 10426328 | 99 | C08 | A09 | 2171.77 | | |
| 7 | | Active | AGAN | DESI | 10748879 | 1 | C01 | B20 | 2121.27 | | |
| 8 | | Active | HUTCHINSON | LLAN | 10683712 | 1 | B20 | C08 | 2040.58 | | |
| 9 | | Active | FRANCIS | DON | 10424547 | 1 | C01 | C08 | 2034.32 | | |
| 10 | | Active | PICKRELL | TRACEE | 10737849 | 34 | A09 | B20 | 2006.66 | | |
| 11 | | Active | FRANZONE | SHAABON | 10420560 | 1 | C01 | B20 | 1978.49 | | |
| 12 | | Active | ABDULLAH | JODIE | 10321040 | 7 | B20 | C08 | 1791.43 | | |
| 13 | | Active | SAWIKI | ENRIQUE | 10687077 | 1 | C08 | A09 | 1611.3 | | |
| 14 | | Active | SHEPARD | KALEN | 10309086 | 1 | B20 | A09 | 1586.97 | | |
| 15 | | Active | SANO | DARREN | 10617876 | 7 | C01 | B20 | 1582.53 | | |
| 16 | | Active | HURLEY | ORVILLE | 10708063 | 1 | B20 | C08 | 1572.49 | | |
| 17 | | Active | GRAHAM | BORIS | 10772267 | 99 | C08 | A09 | 1518.53 | | |
| 18 | | Active | SAUNDERS | WALTON | 10644870 | 1 | B20 | B20 | 1512.22 | | |
| 19 | | Active | APPLEBAUM | EASTER | 10575207 | 8 | B20 | C08 | 1465.3 | | |
| 20 | | Active | SCHWENGINDORF | DEBRA | 10621522 | 1 | C01 | B20 | 1445.91 | | |
| 21 | | Active | HOPE | KAYCE | 10363232 | 8 | C08 | A09 | 1408.9 | | |
| 22 | | Active | BRUSE | AJAMESON | 10636587 | 1 | B20 | A09 | 1370.29 | | |
| 23 | | Active | ROBERTI | VOLKER | 10862195 | 34 | C01 | C08 | 1367.1 | | |
| 24 | | Active | BOOTH | LESLIE | 10758969 | 1 | B20 | C08 | 1355.03 | | |
| 25 | | Active | LEDFORD | VIVIAN | 10571214 | 1 | C08 | A09 | 1317.58 | | |
| 26 | | Active | KILBEG | IRV | 10527240 | 99 | C08 | A09 | 1198.45 | | |
| 27 | | Active | FIELDS | MICHELLE | 10632271 | 7 | B20 | C08 | 1190.19 | | |
| 28 | | Active | ABEYS | SUZIE | 10749323 | 8 | B20 | A09 | 1146.66 | | |
| 29 | | Active | PRENDEVILLE | LEESA | 10602837 | 1 | B20 | C08 | 1103.99 | | |
| 30 | | Active | GRAHAM | BORIS | 10663615 | 1 | A09 | C08 | 996.1 | | |
| 31 | | Active | STANZIALE | KATHERINE | 10730653 | 1 | C01 | B20 | 995.74 | | |

SYSTEM AND USER INTERFACE FOR ACQUISITION AND STORAGE OF PATIENT MEDICAL INSURANCE DATA

This application is a continuation of U.S. application Ser. No. 12/173,519, filed Jul. 15, 2008, and entitled "A System and User Interface for Acquisition and Storage of Patient Medical Insurance Data," which claims a priority benefit to provisional application Ser. No. 60/952,045 filed Jul. 26, 2007, by D.P. O'Shea et al, the entirety of which is incorporated by reference herein.

FIELD OF THE INVENTION

This invention concerns a system for acquiring medical insurance coverage information associating medical insurance coverage identifiers with corresponding patient identifiers for use in claim generation and reimbursement in a hospital information system.

BACKGROUND OF THE INVENTION

The Administrative Simplification section of the Health Insurance Portability and Accountability Act (HIPAA) 1996 provides standards for the exchange of information via electronic transactions between health care providers and third-parties involved in the financial settlement of health care claims. The reduction in the administrative costs for processing health care claims has not been realized to the extent Congress intended. The reasons for continued high administrative costs in spite of the standardization of the format and content of the information exchanged are many. The reasons include incomplete integration of information. Legacy provider and payer information systems are limited in their ability to process EDI (Electronic Data Interchange) standard compatible transactions automatically. Data integration is likely to be implemented as hospitals, physicians and health care payers upgrade or replace their legacy information systems. The replacement cycle for such systems is a long one, but newer systems are available that improve interoperability and integration of data exchanged by heterogeneous systems.

Another reason administrative costs have failed to decline is that the anticipated increase in productivity and the resulting decrease in labor costs have been slow to materialize. This is due, in part, to the complexity of the health care payment system, which continues to require human involvement in the medical claims adjudication process. Most hospitals currently use a manual process to enter 35 eligibility response information into their information systems. A manual process is time consuming and prone to keying errors. Some hospitals have attempted to automate insurance eligibility response information data entry via scripting tools. However, the variability of insurance related information received from payer organizations makes comprehensive automation difficult. Hospitals assign different reimbursement plan codes based on information returned by a payer organization, such as a managed care provider name. This data may not be codified and not standardized. This makes text-based comparison difficult. Additionally, exception situations are common and often require human intervention. In some situations, users may need to contact a managed care provider to discuss information returned in a response message. This type of situation makes complete automation difficult. A system according to invention principles addresses these deficiencies and related problems.

SUMMARY OF THE INVENTION

A system is integrated with a hospital information system (HIS) to provide patient health insurance information identifying patient medical insurance eligibility coverage by sorting and parsing hatched electronic transaction message data to ensure accurate billing and account follow up. A system acquires patient medical insurance coverage identification data for use in medical reimbursement claim generation. An acquisition processor acquires medical insurance coverage information associating medical insurance coverage identifiers with corresponding patient identifiers for multiple different patients. A display processor initiates generation of data representing at least one display image for presenting an acquired medical insurance coverage identifier and corresponding patient identifier and enabling a user to initiate storage of the medical insurance coverage identifier in a record associated with the patient identifier in a healthcare information system. A communication processor initiates communication of the medical insurance coverage identifier for storage in the record associated with the patient identifier in a healthcare information system in response to a command received using the at least one display image.

DETAILED DESCRIPTION OF THE INVENTION

A system is integrated with a hospital information system (HIS) to provide patient health insurance information identifying patient medical insurance eligibility coverage by sorting and parsing hatched electronic transaction message data to provide information to an HIS to facilitate accurate billing and account follow up. The system advantageously supports data integration and improved productivity and enables a user to select data indicating a patient in a window in a User Interface (UI) display image and to display additional data and navigate and incorporate data into an HIS in response to user selection of a displayed button. The system automatically and in one embodiment, in response to user command, organizes and interprets information received electronically including data indicating patient insurance coverage and facilitates user information update of an HIS.

Hospitals typically create batches of patient eligibility inquiries for the purpose of determining insurance coverage. This is especially commonplace in hospitals that serve large Medicaid patient populations. These patients frequently apply for hospital services without their Medicaid identification cards, resulting in incorrect self-pay classification. Other times, patients become Medicaid-eligible after discharge from a hospital, again resulting in incorrect self-pay classification. Hospitals send batches of patient eligibility inquiries electronically to check self-pay patients for Medicaid eligibility. Information returned from Medicaid for those patients with active coverage needs to be input into an HIS in order to initiate Medicaid billing. In known systems, this information is typically entered manually via labor-intensive keying that involves input of lengthy Medicaid identification and group numbers. Additionally, changing patient insurance plan code assignment needs to be done correctly, often varying with information returned in a Medicaid eligibility response message. Further, a Medicaid system may send additional information regarding TPL (Third Party Liability) that is, indicating other health insurers with which the patient has coverage. For patients participating in a Medicaid Health Maintenance Organization (HMO), an eligibility response message may contain information about a Managed Care Plan (MCP), and Primary Care Provider (PCP). The system facilitates the interpretation and entry of the insurance related information and aids incorporation of insurance eligibility response data into an HIS. The system interprets coded data in an eligibility response message and presents the data in an easy-to-read format and facilitates user navigation within HIS display images as well as user copy and paste actions to automatically input lengthy Medicaid identification and group numbers, thereby minimizing data entry errors.

A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled to any other processor enabling interaction and/or communication therebetween. A display processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI). as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps (e.g., of FIG. 8) herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A workflow processor, as used herein, processes data to determine tasks to add to or remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams.

Figure 1:
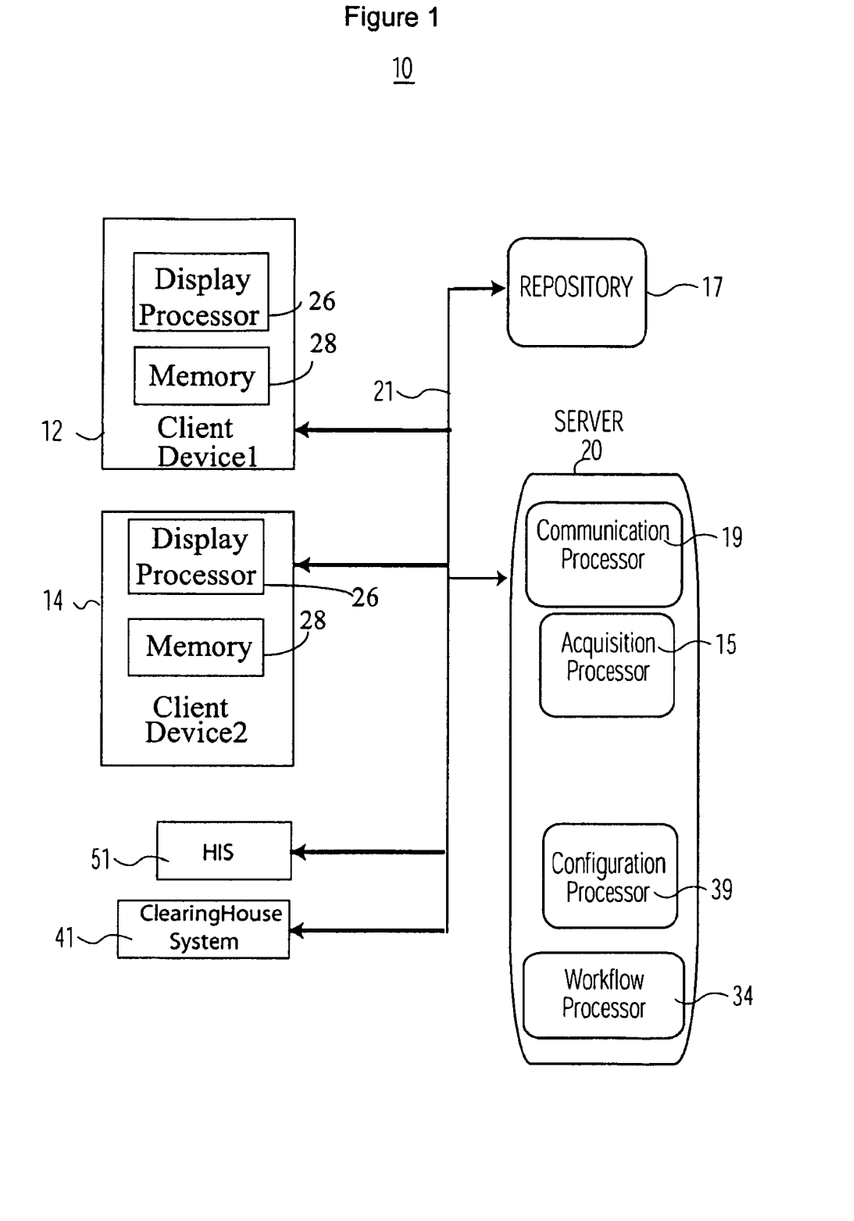
FIG. 1 shows a system for acquiring patient medical insurance coverage identification data for use in medical reimbursement claim generation, according to invention principles.

FIG. 1 shows system 10 for acquiring patient medical insurance coverage identification data for use in medical reimbursement claim generation. System 10 includes a processing device (e.g., workstation or portable device such as a notebook, Personal Digital Assistant, cell phone) 12 (and also 14) that includes a display processor 26. System 10 also includes at least one repository 17 and server 20 intercommunicating via network 21. Display processor 26 provides data representing display images comprising a Graphical User Interface (GUI) for presentation on processing device 12. Acquisition processor 15 acquires medical insurance coverage information associating medical insurance coverage identifiers with corresponding patient identifiers for multiple different patients. At least one repository 17 stores medical insurance coverage information associating medical insurance coverage identifiers with corresponding patient identifiers for multiple different patients.

Display processor 26 initiates generation of data representing at least one display image for presenting an acquired medical insurance coverage identifier and corresponding patient identifier and enabling a user to initiate storage of the medical insurance coverage identifier in a record associated with the patient identifier in healthcare information system (HIS) 51. Communication processor 19 initiates communication of the medical insurance coverage identifier for storage in the record associated with the patient identifier in healthcare information system 51 in response to a command received using the at least one display image. Clearinghouse system 41 processes reimbursement claim data, provided by a healthcare provider organization, to be compatible with requirements of multiple different individual payer organizations. Workflow processor 34 automatically generates an alert message to a worker indicating a patient account is updated. The patient account comprises a record associated with the patient identifier in healthcare information system 51. The alert message indicates the patient account is available for user initiation of generation of a claim for reimbursement for submission to a payer organization associated with the medical insurance coverage identifier.

System 10 is a scalable hybrid system comprising an automated executable process as well as user managed functions for accommodating case specific update of patient accounts. The system provides an electronic work list that also supports data entry and provides a user with information needed to make patient account insurance decisions at a glance while allowing user access to detailed insurance benefit information. Display processor 26 employs individual code modules and class modules for providing display images and business logic. Thereby display processor 26 is adaptive and able to display other types of information (e.g., claim status response data) without modification to navigation logic. Repository 17 stores EDI (Electronic Data Interchange) compatible X12 code and description values for Eligibility Benefits claim segments. The codes and descriptions are expandable in individual sheets or tables to include additional codes and descriptions for a variety of different business purposes.

System 10 is a self-contained system involving combining a spread sheet template file with patient specific response information to provide a composite file, for example. The composite file contains executable code, display processor 26 images, class modules, code and description values and configuration information. The composite file supports easy modification and expandability for a variety of different business purposes. System 10 also employs a configuration file that is read by configuration processor 39 at start-up and determines actions taken in response to activation of navigation buttons and associated displayed button labels. Thereby, a button label may be changed in response to reading the configuration file without requiring programming change. The configuration file also provides target application executable code that may be communicated by communication processor 19 to a Windows-based (or other) application, including applications run under terminal emulation software. Further, processor 19 communicates data derived from the configuration file to a target application in response to user selection of a navigation button. Similarly, communication processor 19 sends data representing literals (a literal is a programming value written exactly as it is meant to be interpreted), action keys such as Enter or Tab, function keys, and patient-specific response data to the target application in response to a configurable delay between actions allowing for timing required by the target application. Thereby system 10 facilitates supportability and deliverability as well as providing a framework for modification for additional uses.

System 10 integrates a source of patient health insurance information (e.g., a database in clearinghouse system 41 or other source) with a hospital information system (HIS) 51. The system in one embodiment acquires multiple ANSI (American National Standards Institute) X12 271 Eligibility transactions for storage in repository 17. The X12 271 transaction is a HIPAA (Healthcare Information Portability Accountability Act) compliant data format used to transport Eligibility Benefit information for health insurance institutions such as Medicaid, Medicare, Aetna, Blue Cross etc. In response to acquisition processor 15 acquiring an X12 271 compatible transaction, processor 15 parses, interprets and translates the 271 transaction into meaningful, readable data elements that are relevant to a user such as; Recipient ID, Date of Service, Coverage Status, Managed Care Information, Co-pay Amount, Deductible, Primary Care Physician etc. The relevant data elements from the 271 transaction are displayed in a Display processor 26 image window that resides at the lower right hand corner of a UI image window, for example. The UI image window allows multiple application windows to be displayed at once, including a HIS patient management application or patient accounting application window, for example. A user at a hospital business office has the ability to determine at a glance via the UI image if a patient account needs to be updated based on eligibility information received from the acquired (e.g., derived from a Payer organization) 271 response transaction.

Figure 2:
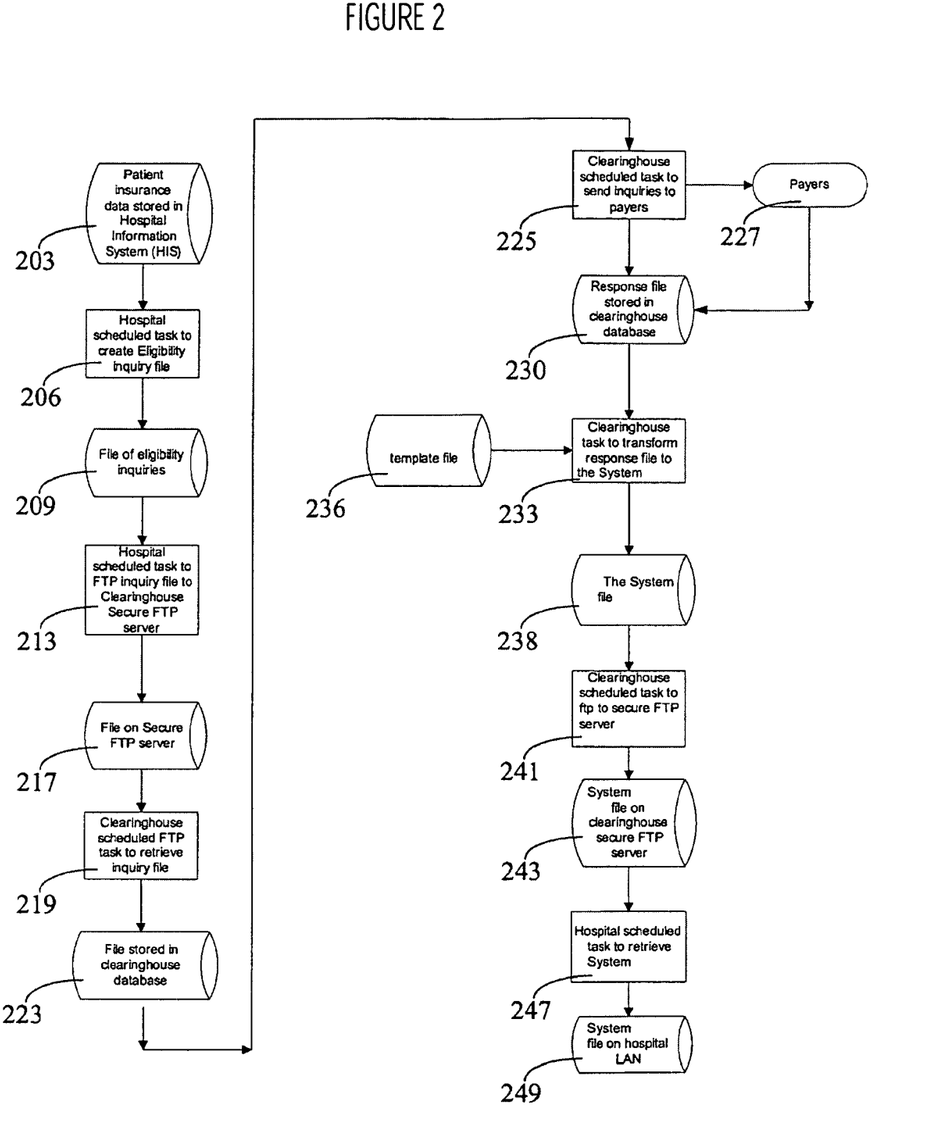
FIG. 2 shows a flowchart of a workflow task sequence of a system for processing patient medical insurance coverage identification data for use in medical reimbursement claim generation, according to invention principles.

FIG. 2 shows a flowchart of an automated workflow task sequence of a system for processing patient medical insurance coverage identification data for use in medical reimbursement claim generation directed by workflow processor 34 (FIG. 1). System 10 in step 203 stores patient insurance related data in repository 17 accessible by HIS 51. In step 206 a hospital schedules a task to create an insurance eligibility inquiry file comprising a list of selected patients that require insurance eligibility verification by HIS 51 and outputs demographic information for the selected patients to a batch file (an inquiry batch file 209). In step 213, the hospital schedules an automated (e.g., via FTP—File Transfer Protocol) transfer of the inquiry batch file to clearinghouse 41 (e.g., HDX) via a secure FTP server 217. Clearinghouse 41 is an intermediary organization that processes inquiries concerning patient insurance eligibility for forwarding to insurance/payer organizations and processes responses from these organizations for return to requesting organizations. In step 219, clearinghouse 41 schedules a process to read the inquiry batch file and convert and format eligibility inquiries derived using the file into a standard EDI (Electronic Data Interchange compatible) message format (e.g. X12 270) for storage in a clearinghouse database 223. In step 225 clearinghouse 41 schedules a task to communicate the formatted eligibility inquiries to payer organizations 227 identified in associated respective individual patient records in the inquiry batch file. A response file from the payer organization is stored in a database in clearinghouse 41 in step 230.

Clearinghouse 41 in step 233 initiates a task to transform insurance eligibility inquiry response messages stored in step 230 in a standard EDI format (e.g., X12 271) from individual payer organizations. Specifically, clearinghouse 41 initiates a task to transform insurance eligibility inquiry response message data using Visual Basic Application (VBA) executable code, for example and using template file 236 to provide transformed response message data in a response batch file 238. Clearinghouse 41 transforms the response batch file 238 to be compatible with a requesting organization format or in another embodiment to be compatible with an acquisition processor 15 data format comprising, an electronic spreadsheet (e.g., employing a Microsoft Excel workbook) containing one row of response data for each patient in the inquiry batch file. Display processor 26 provides a display image for controlling tasks performed in response to user selection of an action button.

Figure 4:
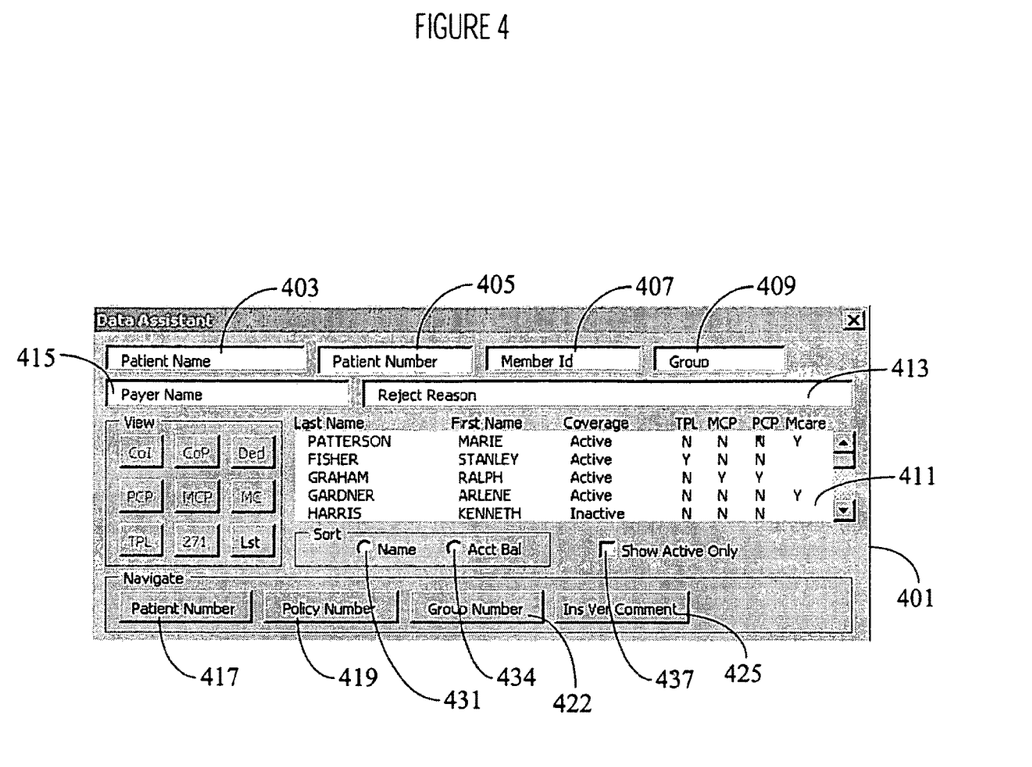
FIGS. 4 and 5 illustrate UI display images employed in processing patient medical insurance coverage identification data, according to invention principles.

FIGS. 4 and 5 illustrate UI display images provided in a system for processing patient medical insurance coverage identification data. User interface display image 401 (FIG. 4) illustrates an initial system start-up image. Selecting a particular patient in main window list box 411 updates Patient Name 403, Patient Number 405, insurance Member Identifier 407, Group 409, Payer Name 415 and Reject Reason 413 text boxes with the information of the particular patient. Image 401 is updated with appropriate enabled buttons in response to type of information selected for display. A user may access information in response to user selection of navigation buttons including, patient number information (button 417), policy number information (button 419), insurance group number information (button 422) and insurance verification comments (button 425). Further, a user may sort information displayed in window 411 by patient name 431, account balance 434 and active or inactive status of patients 437.

User interface display image 501 (FIG. 5) illustrates presentation of patient specific insurance information in boxes 403, 405, 407, 409, 413 and 415 in response to user selection of patient (Ralph Graham) in row 520 of scrolling window 411. Image display 501 includes features that facilitate user action to ensure accurate billing. Display image 501 presents buttons, in view access window 527, including, for example, TPL (Third Party Liability) button 536, MCP (Managed Care Plan) button 525, PCP (Primary Care Provider) button 523, and Medicare coverage button 531. These buttons enable a user to initiate presentation of Third Party Liability, Managed Care Plan, Primary Care Provider and Medicare information for individual patients, respectively. In response to user selection of a particular patient, appropriate buttons in view access window 527 are enabled (inactive buttons remain grey), indicating to the user that additional data is available. In response to user selection of patient (Ralph Graham) in row 520 of window 411, PCP button 523, MCP button 525, Form 271 button 534 and Lst button 529 are enabled. In response to user selection of PCP button 523, secondary window 701 of FIG. 7 is displayed.

Figure 7:
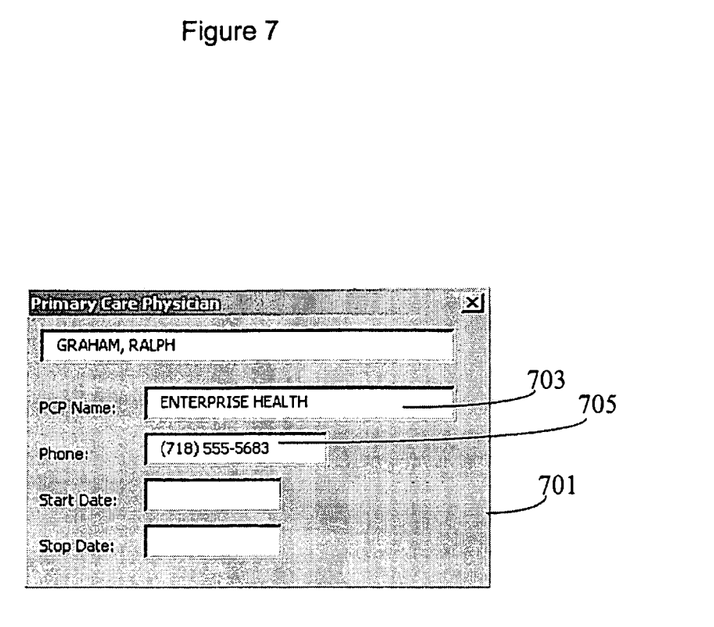
FIG. 7 illustrates a UI pop-up menu for accessing acquired insurance eligibility coverage related information, according to invention principles.

FIG. 7 shows UI pop-up menu 701 for accessing acquired insurance eligibility coverage related information, specifically, Primary Care Physician (PCP) information for the selected patient (Ralph Graham). A user is able to contact a PCP 30 using PCP contact information items 703 and 705 as required by hospital procedures and circumstances.

Figure 5:
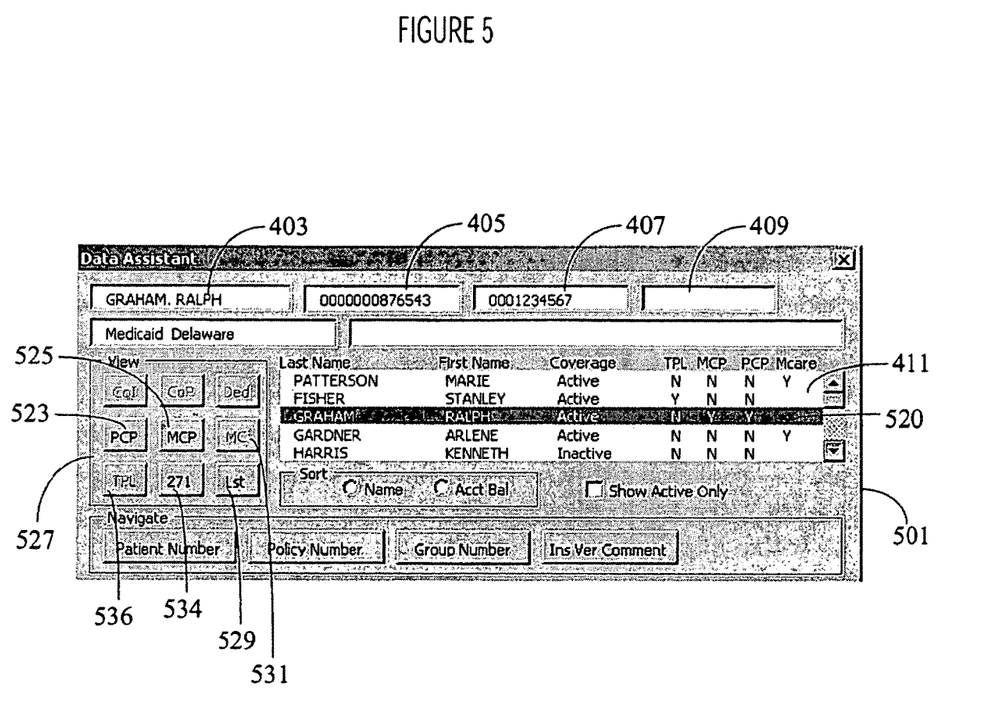
Figure 6:
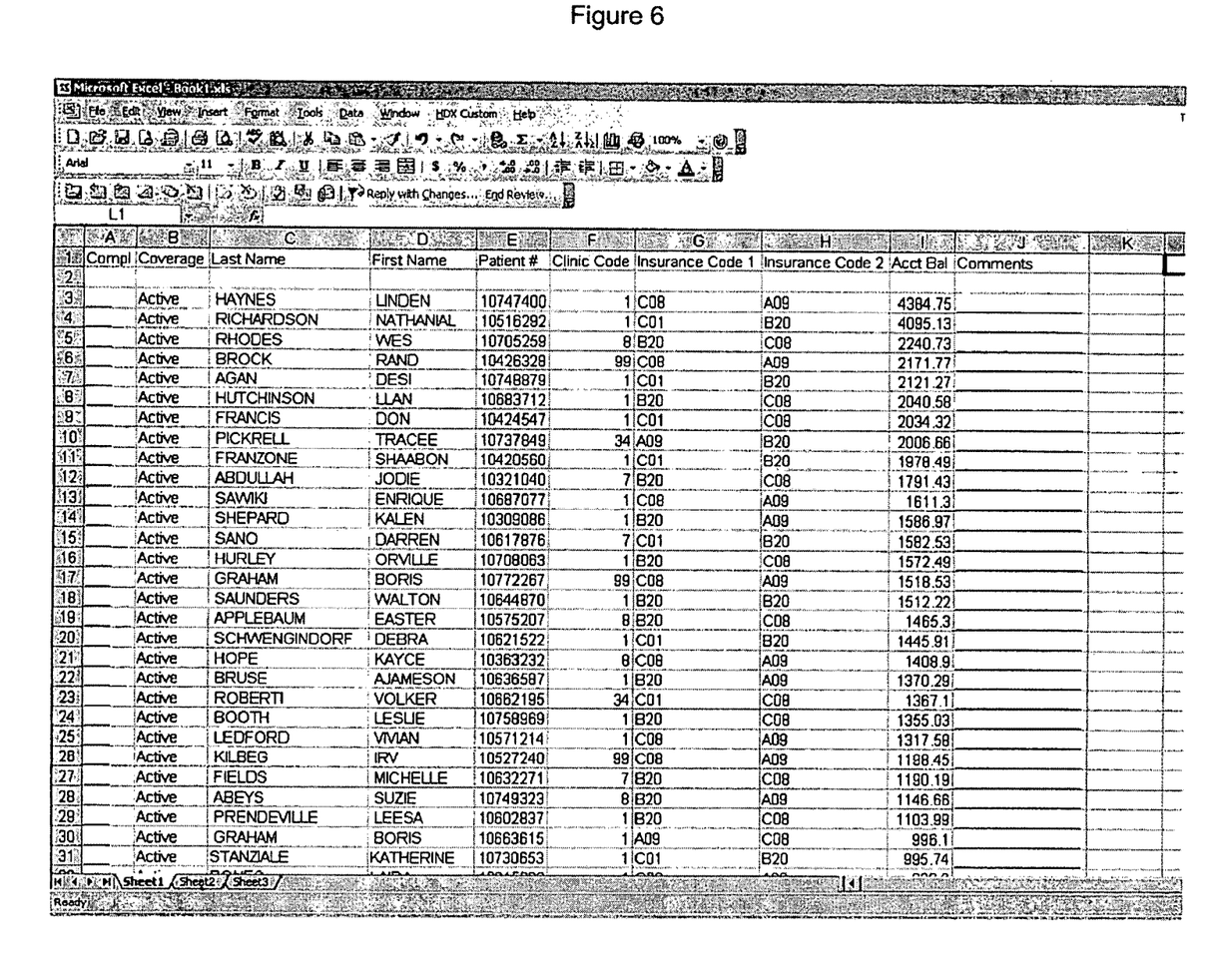
FIG. 6 illustrates a UI presenting acquired insurance eligibility coverage information provided in a system for processing patient medical insurance coverage identification data, according to invention principles.

FIG. 6 illustrate a UI presenting acquired insurance eligibility coverage information provided in a system for processing patient medical insurance coverage identification data presented in response to user selection of Lst button 529 (FIG. 5). Lst button 529 initiates generation of the separate spreadsheet of FIG. 6 including information (a printable work list) concerning individual patients. The function and properties of Lst button 529 are set in response to a user determined configuration file. In response to user selection of Account Balance button 434 (FIG. 4) and Active Coverage Only button 437 and selection of the Lst button, the FIG. 6 spreadsheet report is generated by system 10 (FIG. 1) including the data elements (completion, coverage, last and first names, patient number, clinic code, insurance code, account balance and comments) of the following list.

worklist.Compl=" "
worklist.Coverage=csvField 33
worklist.Last Name=csvField 12
worklist.First Name=csvField 14
worklist.Patient #=csvField 40
worklist.Clinic Code\Insurance Code 1\Insurance Code 2=csvField 47
worklist.Acct Bal=csvField 43 worklist.Comments=" "

The system incorporates EDI X12 compatible code description interpretation and supports other transaction sets, including, 276/277 Claim Status, 837/835 Claim/Remittance and 834 Enrollments.

Continuing with the process of FIG. 2, in step 241, clearinghouse 41 uses FTP in automatically transferring the response batch file 238 to a secure FTP server 243. In step 247 the hospital requesting the insurance eligibility information retrieves response batch file 238 from secure FTP server 243 and stores it as file 249 in repository 17 (FIG. 1) accessible via network 21 (e.g., a LAN and Internet).

In one embodiment, a hospital user of system 10 initiates execution of a patient management or patient accounting module in HIS 51 and initiates operation of system 10 for acquiring patient medical insurance coverage identification data for use in medical reimbursement claim generation. For this purpose an Auto-Open macro executes initiating operation of display processor 26 which generates display images such as the images of FIGS. 4, 5 and 7 using response insurance eligibility information (e.g., response batch file 238 of FIG. 2) provided by clearinghouse 41. Scrolling window 411 (FIG. 4) of image display window 401 incorporates information for the individual patients identified in the response insurance eligibility information.

In response to user selection of a patient in window 411 (FIG. 4), navigation using a patient number look-up function or user selection of a Patient Number action button, in image display window 401, workflow processor 34 directs system 10 actions based on user-determined configuration data in repository 17. For example, in response to user selection of Patient Number button 405 of image display window 401 (FIG. 4), a patient number of a selected patient in window 411 is communicated by processor 19 to HIS 51 (FIG. 1). Workflow processor 34 directs HIS 51 to acquire insurance data concerning the selected patient and directs display processor 26 to navigate and present the data in an Insurance information image. The user sets an HIS insurance verification flag and insurance plan code to be incorporated in the patient record in response to acquiring the insurance information of the selected patient.

In response to user selection of Member identifier button 407, in image display window 401, communication processor 19 communicates a member identifier from insurance eligibility response data acquired from clearinghouse 41 to HIS 51 as directed by workflow processor 34 based on configuration data in repository 17. Similarly, in response to user selection of Group Number button 409, in image display window 401, communication processor 19 communicates a group number from insurance eligibility response data acquired from clearinghouse 41 to HIS 51 as directed by workflow processor 34 based on configuration data in repository 17. A user continues selecting patients in window 411 for communication of response data to HIS 51.

Acquisition processor 15 (FIG. 1) dynamically parses, sorts and analyzes transaction messages from clearing house 41 to facilitate management of high volumes of transaction message data. For instance, if a user is interested in Payer organization response messages indicating "Active" patient insurance coverage, a user selects the "Active Only" button 437 (FIG. 4), thereby displaying records with the Coverage Status of Active. A user is also able to create custom work lists indicating insurance data related tasks that are displayed in an Excel worksheet. The work lists may be created and modified dynamically by updating a configuration file.

Acquisition processor 15 acquires translated payer 271 response messages from a clearinghouse 41 database by selecting a displayed highlighted transaction row in window 411 (FIG. 4) and selecting button 534. In an embodiment in which only a sub set of the full 271 response message is available in local storage, this advantageously provides additional information such as Payer specific free text messages or Benefit limitations information, for example.

In response to a determination that a patient account needs to be updated with new insurance information, communication processor 19 communicates keystrokes and data elements acquired from a 271 transaction message to HIS 51 that a user is logged on to. A user is able to use Navigate command buttons (417, 419, 422 and 425) of display image 401 (FIG. 4) to launch commands that access a patient account and incorporate patient and policy identifiers, group numbers, PCP information, comments etc. The navigation button functions are determined by a configuration file providing a user with flexibility in creating a workflow that is tailored to a user environment and business needs and substantially reduces keying errors and data entry fatigue. System 10 is scalable and merges automated aspects of an executable process with user manual interaction for updating patient accounts.

System 10 in one embodiment comprises a Java (or other programming language) based program, for example, that reads response message information provided by clearinghouse 41 in response to a request for insurance eligibility information. The response message information for an individual patient is placed in a row in a spreadsheet, for example. System 10 is employed in a hospital and in one embodiment comprises a spreadsheet that includes multiple sheets of X12 code description values. Code description value pairs are used to display Eligibility Benefit segment information, such as Co-Insurance, Co-Pay, and Deductible information to a user. An individual sheet of a spreadsheet contains rows of eligibility response information for each inquiry in an inquiry file. A further sheet contains the settings for a configuration file that controls Navigation button (e.g., buttons 417, 419, 422 and 425 of FIG. 4) functions. A row of the spreadsheet contains two columns of information. The first column is used to store common pieces of data supplied by clearinghouse 41 in eligibility information. This information is separated by commas. The second column contains complete EDI X12 271 response message data for a patient. Visual Basic for Applications (VBA) code Forms are used to display images such as those of FIGS. 4, 5 and 7 as well as the sub-forms used to display Coinsurance, Copay, Deductible, Third-Party Liability (TPL) data. Various additional Modules employ VBA code to controls functions including an Auto_Open macro which runs automatically in response to user activation of system 10 to launch the image display of FIG. 4, for example.

Figure 3:
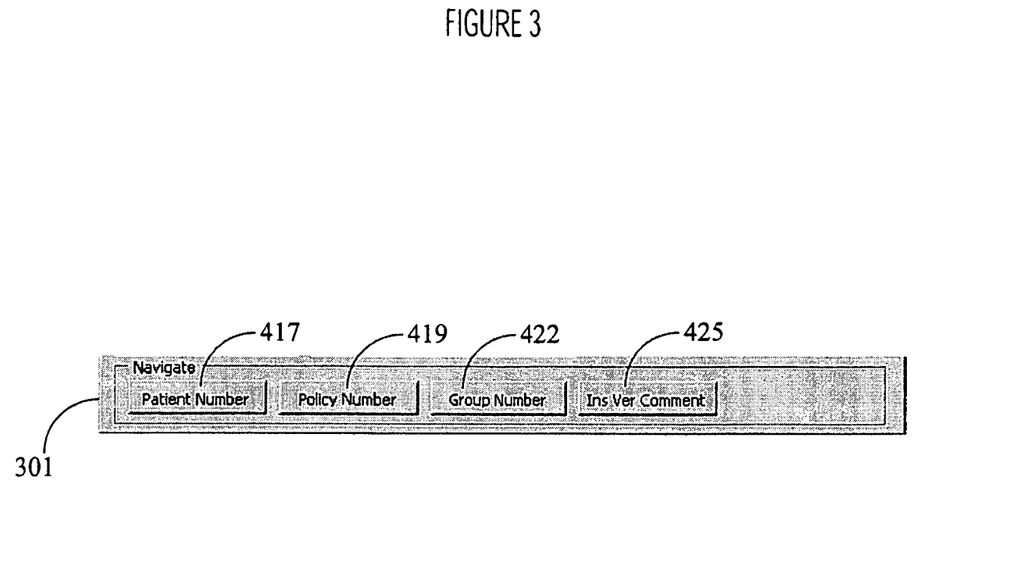
FIG. 3 illustrates configurable User Interface (UI) buttons in a UI provided in a system for processing patient medical insurance coverage identification data, according to invention principles.

At startup, system 10 reads a configuration file that determines the function and labels of displayed Navigation panel buttons of image display 301 (FIG. 3 and also in image display 401 of FIG. 4). A user is able to modify the configuration file to add or remove buttons and determine associated commands. The configuration file determines individual button properties including button Caption (a label displayed on a button), ScreenTitle (a title of the image display incorporating the buttons) and key strokes (a list of comma-separated commands) associated with the buttons. The commands include enter (the enter key), tab (the tab key) wait xx (where xx is any two digit number and causes an application to wait xx seconds before sending data representing the next keys in a command string, e.g., wait 01 would pause 1 second), csvFieldxx (where xx is 01-96, causes an application to send a value of a designated csv field for the selected patient, e.g., csvField40 would send patient number), a function key (e.g., {F3} to send function key 3 and a literal, e.g., "IN"SC" sends INSC).

Data comprising a configuration file used to display a Navigation button panel is,
    cmdButton 1Caption=Patient Number
    cmdButton 1ScreenTitle=TN3270
    cmdButton1SendKeys=csvField 40,enter,wait 01,{F3},
wait 01,{F3},wait 01,tab
    cmdButton2Caption=Policy Number
    cmdButton2ScreenTitle=TN3270
    cmdButton2SendKeys=csvField 27,tab, enter
    cmdButton3Caption=Group Number
    cmdButton3ScreenTitle=TN3270
    cmdButton3SendKeys=csvField 29,tab, enter
    cmdButton4Caption=Ins Ver Comment
    cmdButton4ScreenTitle=TN3270
    cmdButton4SendKeys={F3},wait 01,tab,tab,"INSC",
wait 01,enter System 10 (FIG. 1) provides a link to an executable application provided by clearinghouse 41 acting as an intermediary between a healthcare provider organization and a payer organization in acquiring and forwarding insurance eligibility application. Selection of a patient in window 411 (FIG. 4) provided by display processor 26 (FIG. 1), initiates execution of the clearinghouse eligibility application using a Preview Response function for the selected patient. The preview function pops up a new browser window displaying a patient response. Thereby a user may view available information for a patient in a convenient, easy to read format. System 10 presents a patient response in a familiar browser user interface.

In an alternative embodiment, a hospital creates a report identifying patients for whom Claim Status information is required. The hospital schedules automatic transfer of Claim Status inquiries in the report to a secure ftp server of clearinghouse 41. Clearinghouse 41 formats the report into EDI X12 276 Claim Status inquiry format and sends a batch file to a payer organization for processing. Upon clearinghouse 41 receiving 277 format Claim Status response messages, clearinghouse 41 formats the 277 Claim Status response message batch to create a file for use by system 10 and communication to a hospital. A system 10 user sorts response messages by Claim Status Category Code and also inputs Claim Status response information, via display images provided by display processor 26, for input into a Patient Accounting system and initiates appropriate follow-up action.

Figure 8:
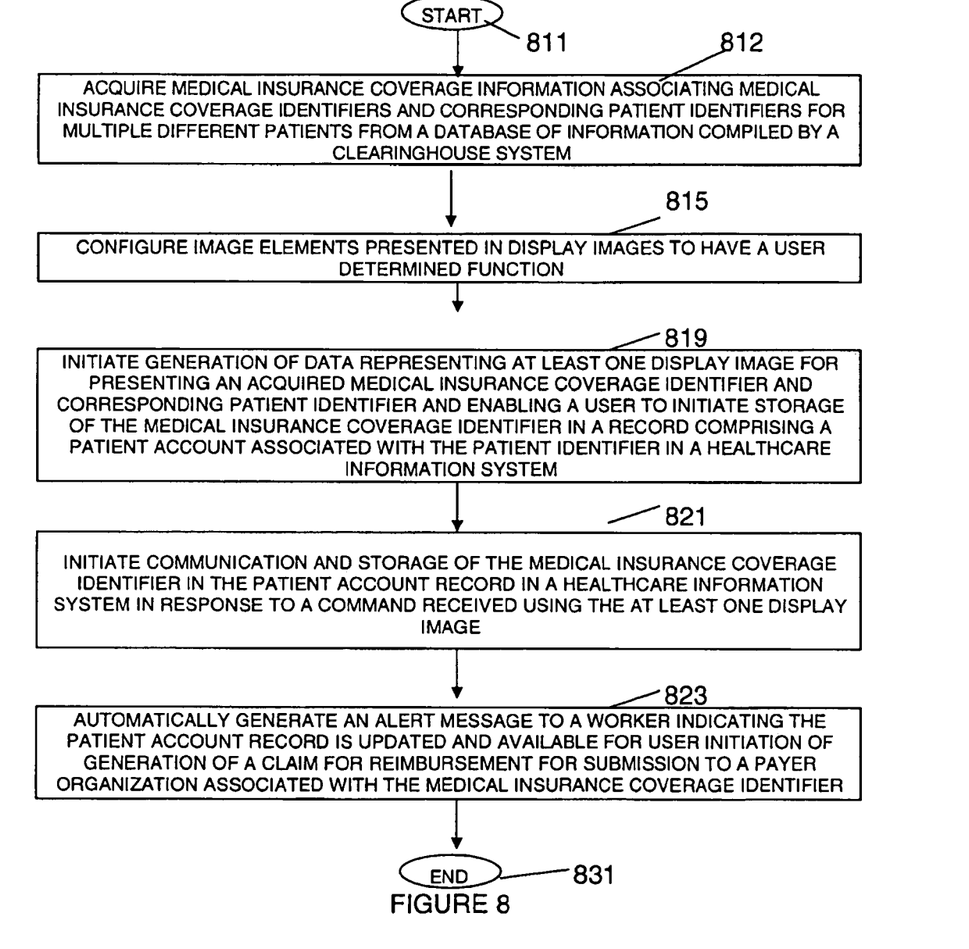
FIG. 8 shows a flowchart of a process performed by a system for acquiring patient medical insurance coverage identification data for use in medical reimbursement claim generation, according to invention principles.

FIG. 8 shows a flowchart of a process performed by system 10 for acquiring patient medical insurance coverage identification data for use in medical reimbursement claim generation. In step 812 following the start at step 811, acquisition processor 15 (FIG. 1) acquires medical insurance coverage information (and medical reimbursement claim status information) associating medical insurance coverage identifiers with corresponding patient identifiers for multiple different patients from a database of information compiled by clearinghouse system 41. Clearinghouse system 41 is used to process reimbursement claim data, provided by a healthcare provider organization, to be compatible with requirements of individual payer organizations and to submit processed reimbursement claim data to a payer organization and process response data responsive to corresponding submitted reimbursement claim data, provided by a payer organization, to be compatible with requirements of a healthcare provider organization. Acquisition processor 15 acquires the medical insurance coverage information, derived from the database of information compiled by clearinghouse system 41, in Electronic Data Interchange (EDI) format transaction messages. In step 815, configuration processor 39 enables a user to configure image elements presented in at least one display image to have a user determined function.

Clearinghouse system 41 processes reimbursement claim data, provided by the healthcare provider organization, to be compatible with requirements of multiple different individual payer organizations. Further, clearinghouse system 41 interrogates multiple different individual payer organizations to acquire one or more medical insurance coverage identifiers of one or more individual patients in response to a first patient identifier (e.g., a social security number) and absence of any medical insurance coverage identifier information for the individual patient. Display processor 26, in step 819, initiates generation of data representing at least one display image for presenting an acquired medical insurance coverage identifier (and acquired medical reimbursement claim status information) and corresponding patient identifier and enabling a user to initiate storage of the medical insurance coverage identifier (and medical reimbursement claim status information) in a record comprising a patient account associated with the patient identifier in healthcare information system 51. The record associated with the patient identifier in healthcare information system 51 comprises a patient account record and the patient account record is updated to include the medical insurance coverage identifier in the patient account record in response to a command received using the at least one display image. In step 821, communication processor 19 initiates communication and storage of the medical insurance coverage identifier (and medical reimbursement claim status information) in the patient account record in healthcare information system 51 in response to the command received using the at least one display image.

Workflow processor 34, in step 823, automatically generates an alert message to a worker indicating the patient account record is updated and available for user initiation of generation of a claim for reimbursement for submission to a payer organization associated with a medical insurance coverage identifier. Workflow processor 34 also automatically initiates generation of a claim for reimbursement for submission to a payer organization associated with the medical insurance coverage identifier. The process of FIG. 8 terminates at step 831.

The systems and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 10 is integrated with HIS 51 for multiple business purposes including acquiring insurance eligibility data and processing claim status responses, remittance responses, or notifications and referral responses. System 10 is usable in any business process that involves viewing patient data and communicating information for the patient to HIS 51. The processes and applications may, in alternative embodiments, be located on one or more (e.g., distributed) processing devices accessing a network linking the elements of FIG. 1. Further, any of the functions and steps provided in FIGS. 1-8 may be implemented in hardware, software or a combination of both and may reside on one or more processing devices located at any location of a network linking the elements of FIG. 1 or another linked network, including the Internet.

What is claimed is:

1. A system for acquiring patient medical insurance coverage identification data for use in medical reimbursement claim generation, comprising:
    a receiving component for receiving a batch of patient insurance eligibility inquiries from at least one requesting organization, the patient insurance eligibility inquiries identifying payer organizations in association with respective individual patient records;
    a clearinghouse system for:
    transforming the batch of patient insurance eligibility inquiries from a first data format, compatible with the receiving component, into a second data format, wherein the second data format is one of a plurality of different data formats, compatible with at least one payer organization, for forwarding to the at least one payer organization;
    forwarding, to the at least one payer organization, the batch of patient insurance eligibility inquiries;
    receiving at least one response from the at least one payer organization from the forwarded batch of patient insurance eligibility inquiries, the at least one response comprising medical insurance coverage information and associating at least one medical insurance coverage identifier with at least one corresponding patient identifier;
    transforming the at least one response from the at least one payer organization, from the second data format into the first data format; and
    returning, to requesting organizations, the at least one response received from the at least one payer organization in the first format;
    a displaying component for displaying the at least one response from the at least one payer organization into a human readable format and representing the at least one medical insurance coverage identifier as a single display image; and
    a transferring component for, in response to a command received using an executable operation, automatically storing the at least one medical insurance coverage identifier in a patient record in a healthcare information system without transcribing the at least one medical insurance coverage identifier, wherein the patient record is associated with the at least one corresponding patient identifier, wherein the executable operation is initiated through user selection of at least one display image.

2. The system of claim 1, wherein the medical insurance coverage information is derived from a database of information compiled by the clearinghouse system.

3. The system of claim 1, wherein the medical insurance coverage information is received in Electronic Data Interchange (EDI) format transaction messages.

4. The system of claim 1, further comprising a configuration processor configured to enable a user to configure image elements presented in at least one display image to have a user determined function.

5. The system of claim 1, wherein the patient record comprises a patient account record that is updated to include the at least one medical insurance coverage identifier in response to the command received using at least one display image.

6. The system of claim 5, wherein the displaying component employs individual code modules and class modules for providing the at least one display image.

7. The system of claim 1, further comprising a workflow processor for automatically generating a claim for reimbursement for submission to the at least one payer organization associated with the at least one medical insurance coverage identifier.

8. The system of claim 1, further comprising a configuration processor configured to read a configuration file at start-up and determine actions taken in response to activation of navigation buttons and associated displayed button labels.

9. The system of claim 8, wherein the configuration file provides a target application executable code.

10. The system of claim 1, wherein the transferring component is further configured to communicate a target application executable code to an application.

11. The system of claim 10, wherein the application is one of a Windows-based application and an application run under a terminal emulation software.

12. A method for acquiring patient medical insurance coverage identification data for use in medical reimbursement claim generation, the method comprising:
receiving a batch of patient insurance eligibility inquiries from at least one requesting organization, the patient insurance eligibility inquiries identifying at least one payer organization in association with at least one patient record;
transforming the batch of patient insurance eligibility inquiries from a first data format into a second data format, wherein the second data format is one of a plurality of different data formats, compatible with the at least one payer organization, for forwarding to the at least one payer organization;
forwarding, to the at least one payer organization, the batch of patient insurance eligibility inquiries;
receiving at least one response from at least one payer organization, the at least one response comprising medical insurance coverage information and associating at least one medical insurance coverage identifier with at least one corresponding patient identifier;
transforming the at least one response from the at least one payer organization, from the second data format into the first data format; and
returning, to the at least one requesting organization, the at least one response received from the at least one payer organization in the second data format;
displaying the at least one response from the at least one payer organization into a human readable format and representing the at least one medical insurance coverage identifier as a single display image; and
enabling a user to automatically store the at least one medical insurance coverage identifier in a record associated with the at least one corresponding patient identifier in a healthcare information system without transcribing the at least one medical insurance coverage identifier, in response to a command received using an executable operation, wherein the executable operation is initiated through user selection of at least one display image.

13. The method of claim 12, wherein the medical insurance coverage information is received in Electronic Data Interchange (EDI) format transaction messages.

14. The method of claim 12, further comprising enabling the user to configure image elements presented in at least one display image to have a user determined function.

15. The method of claim 12, wherein the at least one patient record comprises a patient account record that is updated to include the at least one medical insurance coverage identifier in response to the command received using at least one display image.

16. The method of claim 5, wherein providing the at least one display image further comprises employing individual code modules and class modules.

17. The method of claim 12, further comprising automatically generating a claim for reimbursement for submission to the at least one payer organization associated with the at least one medical insurance coverage identifier.

18. A method comprising:
storing patient insurance related data in a repository, the patient insurance related data comprising insurance eligibility verification, wherein the repository is accessible by a healthcare information system (HIS);
receiving, at the HIS, a request from at least one requesting organization for insurance eligibility verification for at least one patient;
determining that, for the at least one patient, the repository lacks the insurance eligibility verification;
creating an insurance eligibility inquiry file, wherein the insurance eligibility inquiry file comprises a list including the at least one patient;
outputting demographic information for the at least one patient to the insurance eligibility inquiry file; and
automatically transferring the insurance eligibility inquiry file to a clearinghouse, wherein the clearinghouse is configured to:
process the insurance eligibility inquiry file for forwarding to a plurality of payer organizations and process responses from the plurality of payer organizations for return to the at least one requesting organization;
transform the insurance eligibility inquiry file into a standard message format for storage in a clearinghouse database;
communicate the insurance eligibility inquiry file to at least one payer organization of the plurality of payer organizations;
receive an inquiry response message from the at least one payer organization;
store the inquiry response message in a database in the clearinghouse; and transform the inquiry response message in the standard message format from individual payer organizations.

19. The method of claim 18, wherein the automated transfer of the insurance eligibility inquiry file is conducted via a secure FTP server.

20. The method of claim 18, wherein the standard message format is an Electronic Data Interchange compatible (EDI) format.

* * * * *

UNITED STATES PATENT AND TRADEMARK OFFICE
CERTIFICATE OF CORRECTION

PATENT NO.         : 11,232,373 B2                                                    Page 1 of 1
APPLICATION NO.    : 16/531724
DATED              : January 25, 2022
INVENTOR(S)        : O'Shea et al.

It is certified that error appears in the above-identified patent and that said Letters Patent is hereby corrected as shown below:

In the Specification

Column 4, Line 3, delete "(UI)." and insert -- (UI), --.

Column 4, Line 43, delete "and or" and insert -- and/or --.

Column 4, Line 48, delete "and or" and insert -- and/or --.

Column 10, Line 24, delete ""IN"SC"" and insert -- "INSC" --.

In the Claims

Column 14, Line 29, in Claim 16, delete "claim 5," and insert -- claim 15, --.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*